US008075926B2

(12) United States Patent
Levine et al.

(10) Patent No.: US 8,075,926 B2
(45) Date of Patent: Dec. 13, 2011

(54) HERBAL COMPOSITIONS FOR THE TREATMENT OF MUCOSAL LESIONS

(75) Inventors: William Z. Levine, Jerusalem (IL); Aron J. Saffer, Beit Shemesh (IL); Mina Fran, Jerusalem (IL)

(73) Assignee: Izun Pharmaceuticals Corporation, Jerusalem (IL)

( * ) Notice: Subject to any disclaimer, the term of this patent is extended or adjusted under 35 U.S.C. 154(b) by 0 days.

(21) Appl. No.: 12/417,106

(22) Filed: Apr. 2, 2009

(65) Prior Publication Data

US 2009/0297641 A1 Dec. 3, 2009

Related U.S. Application Data

(62) Division of application No. 10/478,718, filed as application No. PCT/IL02/00402 on May 22, 2002, now Pat. No. 7,563,466.

(30) Foreign Application Priority Data

May 23, 2001 (IL) .......................................... 143318

(51) Int. Cl.
*A61K 36/00* (2006.01)
*A61K 36/38* (2006.01)
*A61K 36/82* (2006.01)

(52) U.S. Cl. ......... 424/729; 424/725; 424/730; 424/737
(58) Field of Classification Search ........................ None
See application file for complete search history.

(56) References Cited

U.S. PATENT DOCUMENTS

| 5,162,037 A * | 11/1992 | Whitson-Fischman ......... 600/12 |
| 5,543,154 A | 8/1996 | Rork et al. |
| 5,780,046 A | 7/1998 | Humber et al. |
| 5,834,000 A | 11/1998 | Yng-Wong |
| 5,977,176 A * | 11/1999 | Wise et al. .................... 514/568 |
| 6,039,949 A * | 3/2000 | Pero ............................. 424/769 |
| 6,350,784 B1 * | 2/2002 | Squires ......................... 514/642 |
| 6,428,819 B1 * | 8/2002 | Lavie et al. .................... 424/730 |
| 2003/0003140 A1 | 1/2003 | Domb et al. |
| 2004/0151789 A1 | 8/2004 | Levine et al. |

FOREIGN PATENT DOCUMENTS

| EP | 0 173 092 | 3/1986 |
| JP | 61-165334 | 7/1986 |
| JP | 7-506842 | 7/1995 |
| JP | 10-279468 | 10/1998 |
| JP | 10-279590 | 10/1998 |
| JP | 2000-119188 | 4/2000 |
| JP | 2001-098263 | 4/2001 |
| JP | 2001-505546 | 7/2011 |
| WO | WO 98/11778 | 3/1998 |
| WO | WO9811778 | 3/1998 |
| WO | 98 42188 | 10/1998 |
| WO | WO 99/24009 | 5/1999 |
| WO | WO 01/15553 | 3/2001 |

OTHER PUBLICATIONS

Kornblith (In Vitro Responses of Ovarian Cancers to Platinums and Taxanes, Anticancer Research 23: 543-548 (2003).*
DW ACC 1986-063007, Mar. 1986, EP 173092 A De, Bliah et al.*
"Martindale—The Extra Pharmacopeia, 30$^{th}$ Ed.", 1993, The Pharmaceutical Press, London, XP002211675, 3 pages.
Preparations: Echinacea Rö-Plex, Sambucus Complex, Sinotar, 1993.
Chavez et al; "Saint John's Wort"; Hospital Pharmacy, Lippincott, Philadelphia, US, vol. 32, No. 12, 1997, pp. 1621-1628 and 1631-1632, XP000913486.
Bauer: "Echinacea-Drogen-Wirkungen und Wirksubstanzedn"; Zeitschrift Fuer Aerztliche Fortbildung, Jena, DD, vol. 90, 1996, pp. 111-115, XP000198717.
Serkedjieva et al; "Antiviral Activity of the Infusion (SHS-174) From Flowers of *Sambucus nigra* L., Aerial Aprts of *Hypericum perforatum* L., and Roots of *Saponaria officinalis* L. Against Influenza and Herpes Simplex Viruses"; Phytother Res., vol. 4, No. 3, 1990, pp. 97-100, XP001099138.
Hans Braun: "Heilpflanzen-Lexikon fur Arzte und Apotheker", 1981, Gustav Fisher Verlag, Stuttgart, pp. 68-69, 197-198, 120-121 and 87. XP002211676.
J. Bruneton: "Pharmacognosy Phytochemistry Medicinal Plants"; 1999, Lavoisier Publishing, Paris, pp. 175, 703-704, 441-442 and 366-367, XP002211677.
"Echinacea"; Honest Herbal: A Sensible Guide to the Use of Herbs and Related Remedies, Pharmaceutical Products Press, New York, NY, US, 1993, pp. 115-117, XP002914645.
Brinkhaus et al; "Chemical Pharmacological and Clinical Profile of the East Asian Medical Plant *Centella asiatica*"; Phytomedicine: International Journal of Phytotherapy and Phytopharmacology. Germany, Oct. 2000, vol. 7, No. 5, pp. 427-448, XP002211674.
Page, "Milestones in Periodontal Research and the Remaining Critical Issues," Journal of Periodontal Research, 1999, vol. 34, pp. 331-339.
Serkedijieva et al., "Antiviral Activity of the Infusion (SHS-174) from Flowers of *Sambucus nigra* L., Aerial Parts of *Hypericum perforatum* L., and Roots of *Saponaria officinalis* L. against Influenza and Herpes simplex Viruses," Phytotherapy Research, vol. 4, No. 3, 1990, pp. 97-100.
"Echinacea", The Honest Herbal: A Sensible Guide to the Use of Herbs and Related Remedies, Pharmaceutical Products Press, New York, NY, 1993, pp. 115-117.
Chavez et al., "Saint John's Wort", Hospital Pharmacy, vol. 32, No. 12, pp. 1621-1632, 1997.
Braun, "Heilpflanzen-Lexikon fur Arzte und Apotheker", Gustav Fisher Verlag, Stuttgart, 1981, pp. 68-69, 87, 120-121 and 197-198.
Bruneton, "Pharmacognosy Phytochemistry Medicinal Plants," Lavoisier Publishing, 1999, pp. 173-175, 366-367, 439-442 and 703-704.
Ceschel et al., "Design and Evaluation of Buccal Adhesive Hydrocortisone Acetate (HCA) Tablets", Drug Delivery, vol. 8, pp. 161-171, 2001.

(Continued)

*Primary Examiner* — Christopher R Tate
*Assistant Examiner* — Randall Winston
(74) *Attorney, Agent, or Firm* — Nixon & Vanderhye P.C.

(57) ABSTRACT

The present invention provides therapeutic compositions comprising extracts of the plant species *Echinacea purpurea* and *Sambucus nigra* and the extract(s) of at least one further plant selected from the group consisting of *Hypericum perforatum*, *Commiphora molmol* and *Centella asiatica*. The compositions of the invention are of particular utility in the management of inflammatory mucosal diseases of both viral and non-viral origin.

13 Claims, 3 Drawing Sheets

OTHER PUBLICATIONS

Reply filed in European Patent App. No. 02 733 198.2-2107, including exhibits and appendix attached thereto (May 16, 2007).

Communication in European Patent App. No. 02 733 198.2-2107, including International Preliminary Examination Report and Written Opinion for PCT/IL02/00402.

R. Aquino et al., "Plant Metabolites, Structure and In Vitro Antiviral Activity of Quinovic Acid Glycosides From *Uncaria tomentosa* and *Guettarda Platypoda*", Journal of Natural Products, vol. 52, No. 4, pp. 679-685, Jul.-Aug. 1989.

Blaih et al., DW 1986-063007, Mar. 1986.

"Plant preparations used as ingredients of cosmetic products" 1989 (re-printed 1994) ISBN 92-871-1689-X; published by the Council of Europe.

J. Soc. Cosmet. Chem. Jpn., 1998, vol. 32, No. 3, pp. 272-279.

* cited by examiner

HERBAL COMPOSITIONS FOR THE TREATMENT OF MUCOSAL LESIONS

CROSS RELATED APPLICATION

This application is a divisional of U.S. patent application Ser. No. 10/478,718 filed Nov. 24, 2003, which is a U.S. national phase of international application PCT/IL02/00402, filed in English on 22 May 2002, which designated the US. PCT/IL02/00402 claims priority to IL Application No. 143318, filed 23 May 2001. The entire contents of these applications are incorporated herein by reference.

FIELD OF THE INVENTION

The present invention relates to herbal compositions useful for the treatment of mucosal lesions. Although primarily intended for oral use the composition may also be used on the labial, genital and other mucosal surfaces, as well as on the skin.

BACKGROUND OF THE INVENTION

Historically, the plant world has been the most important source of medicinal agents for the treatment of human and animal disease, and for use as preventative agents in maintaining good health. However, for at least the last 150 years, Western medicine has been dominated by synthetic and/or highly purified chemical agents.

It is now being increasingly recognized, however, that plant extracts may be highly effective agents for the prevention and treatment of disease. This is particularly true when one considers the low toxicity and greatly reduced incidence of adverse effects associated with plant-based medicines as compared with many synthetic or highly purified drugs. In addition, as the plant possesses a large number of pharmaceutically active agents, extracts obtained therefrom exert their activities on a variety of physiologic processes, increasing the range of the desired therapeutic effect.

Although traditional reference sources of herbal medicine are valuable guides to the safe and effective use of plant extracts, the appropriate selection and combination of extracted material is still a major challenge to the development of new, highly effective herbal medicines. The scale of this challenge may be more clearly appreciated when it is realized that there are approximately 750,000 species of flowering plants on earth, only very few of which have been scientifically studied for their potential therapeutic value.

Oral diseases constitute a diverse group of conditions that are responsible for much human suffering. In addition to diseases of the hard tissues of the oral cavity (e.g. dental caries), there are many different pathological conditions affecting the oral mucosa and periodontal tissues. This group includes the commonly found conditions such as gingivitis, periodontal disease, aphthous ulceration and Herpes simplex lesions, as well as the oral manifestations of the less common vesicular-bullous conditions such as bullous pemphigoid, pemphigus, erytheme multiforme and lichen planus, as well as other autoimmune conditions.

The significance of host-related factors in the pathogenesis of conditions such as periodontal disease is being increasingly recognized. Far from being a passive recipient of pathogenic agents released by plaque bacteria, the host tissues themselves (including the biochemical and immunological factors contained therein) are now known to make an active contribution to disease initiation and progression. One group of host factors which have recently received some attention in relation to the pathogenesis of periodontal disease is the group consisting of various tissue-destroying and tissue-remodelling enzymes. Of particular interest is the large group of matrix metalloproteinases (Page, R. C. (1999) J. Periodont. Res. 34: 331-339). It is now believed that certain, defined, metalloproteinases such as matrix metalloproteinases 1-9 are of particular importance for the development and progression of periodontal disease.

Although many pharmaceutical agents have been used in the management of mucosal lesions, many of these have been relatively ineffective, while some (in particular, the systemic regimes) are associated with unacceptable adverse effects. There thus exists a need for new, efficacious and safe modes of treatment for many of the aforementioned mucosal diseases. There is a particular need for a safe, effective topical treatment.

It is a purpose of the present invention to respond to the aforementioned need by providing plant-based compositions for the treatment of mucosal diseases.

It is another purpose of the invention to provide plant-based anti-viral compositions for use in the treatment of oral and genital lesions.

It is a further purpose of the invention to provide compositions for the treatment of mucosal diseases having higher efficacy and more rapid onset than compositions previously known in the art.

It is a still further purpose of the invention to provide compositions having lower toxicity and incidence of adverse effects than pharmaceutical compositions for the treatment of mucosal diseases that have been previously described in the art.

Further objects and advantages of the present invention will become apparent as the description proceeds.

SUMMARY OF THE INVENTION

It has now been unexpectedly found that certain compositions comprising particular combinations of plant extracts are highly effective in the treatment of certain mucosal lesions, particularly those of the oral, anal and genital mucosa, as well as in the treatment of certain skin lesions. It is to be noted that the compositions, medicaments and treatment methods of the present invention which will presently be disclosed, described and exemplified, have been unexpectedly found to cause a dramatic improvement in two significant clinical parameters associated with the mucosal and skin lesions being treated thereby. Firstly, it has been surprisingly found that said compositions, medicaments and treatment methods lead to unexpectedly rapid resolution of the mucosal and skin lesions that are being treated. Secondly, the compositions, medicaments and treatment methods of the present invention have also been surprisingly found to cause a dramatic reduction of the pain associated with the mucosal and skin lesions being treated thereby.

The present invention is primarily directed to a therapeutic composition comprising extracts of the plant species *Echinacea purpurea* and *Sambucus nigra* and the extract(s) of at least one further plant selected from the group consisting of *Hypericum perforatum*, *Commiphora molmol* and *Centella asiatica*.

In one preferred embodiment of the therapeutic composition of the present invention, the extract(s) of the at least one further plant are extracts of the plant species *Hypericum perforatum* and *Commiphora molmol*.

While it is not intended that the use of the composition of the abovementioned preferred embodiment of the composition of the invention be bound to, or limited by any particular theory regarding its chemical or pharmacological mode of action, the present invention is particular directed to an anti-viral composition comprising extracts of the plant species *Echinacea purpurea, Sambucus nigra, Hypericum perforatum* and *Commiphora molmol*.

In a preferred embodiment of the invention, the above-mentioned anti-viral composition further comprises extracts of plants selected from the group consisting of *Uncaria tomentosa, Thymus vulgaris, Matricaria recutita, Salix alba, Calendula officinalis, Usnea barbata, Ligusticum porterii-osha, Gaultheria procumbens, Camellia sinensis, Vaccinium myrtillus, Melissa officinalis, Allium sativum, Camellia sinensis* and *Krameria triandra*.

In a particularly preferred embodiment of the invention, the above-mentioned anti-viral composition comprises extracts of the plant species *Echinacea purpurea, Sambucus nigra, Hypericum perforatum, Commiphora molmol* and *Uncaria tomentosa*.

The present invention also provides a therapeutic composition comprising extracts of the plant species *Echinacea purpurea* and *Sambucus nigra* together with an extract of the plant species *Centella asiatica*.

In a preferred embodiment of the invention, the immediately preceding therapeutic composition is intended for use in the treatment of diseases of the oral mucosa. In a more preferred embodiment of the invention, said therapeutic composition is intended for use in the treatment of an oral mucosal disease selected from the group consisting of periodontal disease, gingivitis, aphthous ulceration, mechanical trauma, thermal trauma, lichen planus, bullous pemphigoid, pemphigus vulgaris, dermatitis herpetiformis, angular chelitis and recurrent herpes.

In a further preferred embodiment, the above therapeutic composition is intended for use in the treatment of skin lesions. In one preferred embodiment of the invention, said therapeutic composition is intended for use in the treatment of dermal trauma. In another preferred embodiment, the therapeutic composition is intended for use in the treatment of insect bites and other local, superficial irritations.

In a still further preferred embodiment of the invention, the above therapeutic composition is intended for use in the treatment of anal lesions. In a more preferred embodiment of the invention, said therapeutic composition is intended for use in the treatment of an anal lesion associated with a condition selected from the group consisting of anal fissures, hemorrhoids and non-specific irritation.

While it is not intended that the mechanism of action of the therapeutic composition for treating mucosal diseases that is disclosed immediately hereinabove be bound to any particular pharmacological or pathophysiological mechanism or mechanisms, it is believed that said composition exerts at least some of its desired effects by inhibiting one or more matrix metalloproteinase (MMP) enzymes that are present in the oral mucosal and periodontal tissues, and/or by increasing collagen production at or close to the mucosal site to which said composition is applied. In particular, it is believed that said therapeutic compositions may exert at least some of their desired effects by the specific inhibition of certain specific enzymes of the MMP group. More specifically, it is believed that the therapeutic compositions of the present invention are specific inhibitors of MMP subclasses 1-9, still more specifically of subclasses 1, 2, 8 and 9.

Thus, the invention is also directed to a therapeutic composition comprising extracts of the plant species *Echinacea purpurea, Sambucus nigra* and *Centella asiatica* described hereinabove, for the inhibition of one or more matrix metalloproteinases.

It is to be noted that the term "inhibition of one or more matrix metalloproteinases" as used immediately hereinabove and hereinabove is intended to convey the meaning of the inhibition of the activity of these enzymes on their substrates.

In a preferred embodiment of this aspect of the invention, the one or more matrix metalloproteinases to be inhibited are selected from the group consisting of matrix metalloproteinases 1-9. In a more preferred embodiment, said one or more matrix metalloproteinases are selected from the group consisting matrix metalloproteinases 1, 2, 8 and 9. Still more preferably, the matrix metalloproteinase to be inhibited is matrix metalloproteinase 2. In a still further preferred embodiment of this aspect of the present invention, the matrix metalloproteinase-inhibiting therapeutic compositions described immediately hereinabove are intended for use in the treatment of a disease of the oral mucosa selected from the group consisting of periodontal disease and aphthous ulceration.

In a further preferred embodiment of the invention, the aforementioned therapeutic compositions for treating conditions of the oral or anal mucosal tissues, as well as the aforementioned therapeutic compositions for inhibiting matrix metalloproteinases further comprise extracts of plants selected from the group consisting of *Uncaria tomentosa, Thymus vulgaris, Matricaria recutita, Salix alba, Calendula officinalis, Usnea barbata, Ligusticum porterii-osha, Gaultheria procumbens, Camellia sinensis, Vaccinium myrtillus, Melissa officinalis, Allium sativum, Camellia sinensis* and *Krameria triandra*.

In another aspect, the present invention is directed to the use of a combination of extracts of the plant species *Echinacea purpurea* and *Sambucus nigra* and of at least one further plant species selected from the group consisting of *Hypericum perforatum, Commiphora molmol* and *Centella asiatica* in the preparation of a medicament.

In one preferred embodiment, the invention is directed to the use of the combination of plant extracts described immediately hereinabove in the preparation of a medicament, wherein said extracts of at least one further plant are extracts of *Hypericum perforatum* and *Commiphora molmol*. Preferably, this combination of plant extracts is used in the preparation of an anti-viral medicament.

In a further preferred embodiment, the present invention is directed to the use of extracts of plants selected from the group consisting of *Uncaria tomentosa, Thymus vulgaris, Matricaria recutita, Salix alba, Calendula officinalis, Usnea barbata, Ligusticum porterii-osha, Gaultheria procumbens, Camellia sinensis, Vaccinium myrtillus, Melissa officinalis, Allium sativum, Camellia sinensis* and *Krameria triandra*, in addition to the extracts mentioned hereinabove, in the preparation of an anti-viral medicament.

In a particularly preferred embodiment the present invention is directed to the use of a combination of extracts of the plant species *Echinacea purpurea, Sambucus nigra, Hypericum perforatum, Commiphora molmol* and *Uncaria tomentosa* in the preparation of an anti-viral medicament.

The present invention also provides for the use of the above combination of plant extracts in the preparation of a medicament, said extract of at least one further plant being an extract of *Centella asiatica*. Preferably, this combination of plant extracts is used in the preparation of a medicament for the treatment of a disease of the oral mucosa. In one embodiment of the invention, said disease of the oral mucosa is selected from the group consisting of periodontal disease, gingivitis, aphthous ulceration, mechanical trauma, thermal trauma, lichen planus, bullous pemphigoid, pemphigus vulgaris, dermatitis herpetiformis, angular chelitis and recurrent herpes.

In another preferred embodiment, the invention also provides for the use of the above combination of plant extracts in the preparation of a medicament for the treatment of a skin lesion. In one preferred embodiment, the skin lesion to be treated is a lesion arising from dermal trauma. In a further preferred embodiment, the skin lesion to be treated is an insect bite.

In another preferred embodiment of the invention, the abovementioned combination of plant extracts is used in the preparation of a medicament for the treatment of a disease of the anal mucosa. In one embodiment of the invention, said disease of the anal mucosa is selected from the group consisting of anal fissures, hemorrhoids and non-specific irritation.

In another aspect the invention provides for the use of a combination of extracts of the plant species *Echinacea purpurea*, *Sambucus nigra* and *Centella asiatica* in the preparation of a medicament for inhibiting one or more matrix metalloproteinases. Preferably, said matrix metalloproteinases are selected from the group consisting of matrix metalloproteinases 1 to 9. Most preferably, the one or more matrix metalloproteinases to be inhibited are selected from the group consisting of matrix metalloproteinases 1, 2, 8 and 9. In a preferred embodiment, the abovementioned metalloproteinase-inhibiting medicament is used to treat a disease of the oral mucosa selected from the group consisting of periodontal disease and aphthous ulceration.

In a further preferred embodiment, the invention is directed to the use of the above combination of plant extracts in combination with further extracts of plants selected from the group consisting of *Uncaria tomentosa*, *Thymus vulgaris*, *Matricaria recutita*, *Salix alba*, *Calendula officinalis*, *Usnea barbata*, *Ligusticum porterii-osha*, *Gaultheria procumbens*, *Camellia sinensis*, *Vaccinium myrtillus*, *Melissa officinalis*, *Allium sativum*, *Camellia sinensis* and *Krameria triandra*, in the preparation of medicaments for the treatment of a diseases of the oral and/or anal mucosal tissues, and in the preparation of medicaments for inhibiting the abovementioned one or more matrix metalloproteinases.

In another aspect, the present invention is directed to a combination of extracts of the plant species *Echinacea purpurea* and *Sambucus nigra* and of at least one further plant species selected from the group consisting of *Hypericum perforatum*, *Commiphora molmol* and *Centella asiatica* for use as a medicament.

In a preferred embodiment, the invention is directed to a combination of extracts as disclosed immediately hereinabove, wherein the extracts of the at least one further plant are extracts of *Hypericum perforatum* and *Commiphora molmol*. In a preferred embodiment, the invention is directed to said combination of extracts for use as an anti-viral medicament. In a further preferred embodiment, said combination of extracts is further supplemented by extracts of one or more plants selected from the group consisting of *Uncaria tomentosa*, *Thymus vulgaris*, *Matricaria recutita*, *Salix alba*, *Calendula officinalis*, *Usnea barbata*, *Ligusticum porterii-osha*, *Gaultheria procumbens*, *Camellia sinensis*, *Vaccinium myrtillus*, *Melissa officinalis*, *Allium sativum*, *Camellia sinensis* and *Krameria triandra*.

In a particularly preferred embodiment, the invention is directed to a combination of extracts of the plant species *Echinacea purpurea*, *Sambucus nigra*, *Hypericum perforatum*, *Commiphora molmol* and *Uncaria tomentosa* for use as an anti-viral medicament.

The invention also provides a combination of plant extracts as disclosed hereinabove for use as a medicament, said extract of the at least one further plant being an extract of *Centella asiatica*. Preferably, this combination of extracts is provided for use as a medicament for the treatment of diseases of the oral mucosa. While said combination of plant extracts may be used as a medicament for the treatment of many different conditions of the oral mucosa, in a preferred embodiment, the disease to be treated is selected from the group consisting of periodontal disease, gingivitis, aphthous ulceration, mechanical trauma, thermal trauma, lichen planus, bullous pemphigoid, pemphigus vulgaris, dermatitis herpetiformis, angular chelitis and recurrent herpes. In another preferred embodiment, the combination of plant extracts is provided for use as a medicament for the treatment of skin lesions. In one preferred embodiment, the skin lesions are lesions arising from dermal trauma. In another preferred embodiment, the skin lesions are insect bites. In yet another preferred embodiment, the aforementioned combination of extracts is provided for use as a medicament for the treatment of diseases of the anal mucosa. While said combination of plant extracts may be used as a medicament for the treatment of many different conditions of the anal mucosa, in a preferred embodiment, the disease to be treated is selected from the group consisting of anal fissures, hemorrhoids and non-specific irritation.

In another aspect, the above-described combination of extracts is used as a medicament for inhibiting one or more matrix metalloproteinases. Preferably, the one or more matrix metalloproteinases are selected from the group consisting of matrix metalloproteinases 1 to 9. More preferably, said metalloproteinases are selected from the group consisting of matrix metalloproteinases 1, 2, 8 and 9. In a preferred embodiment, the abovementioned combination of extracts for inhibiting metalloproteinases is used in the treatment of a disease of the oral mucosa selected from the group consisting of periodontal disease and aphthous ulceration.

In yet another embodiment of the invention, the plant extracts used in the aforementioned combination of extracts are further supplemented by extracts of plants selected from the group consisting of *Uncaria tomentosa*, *Thymus vulgaris*, *Matricaria recutita*, *Salix alba*, *Calendula officinalis*, *Usnea barbata*, *Ligusticum porterii-osha*, *Gaultheria procumbens*, *Camellia sinensis*, *Vaccinium myrtillus*, *Melissa officinalis*, *Allium sativum*, *Camellia sinensis* and *Krameria triandra*.

The present invention also encompasses a method of treatment of mucosal and/or skin lesions comprising the application of a therapeutically-effective amount of a mixture of extracts of the plant species *Echinacea purpurea* and *Sambucus nigra* and the extract(s) of at least one further plant selected from the group consisting of *Hypericum perforatum*, *Commiphora molmol* and *Centella asiatica* to the mucosal lesions and surrounding tissue of a subject in need of such treatment. In a preferred embodiment of this method of treatment, said extracts of at least one further plant are extracts of *Hypericum perforatum* and *Commiphora molmol*. In a preferred embodiment, the lesions to be treated by this method of treatment are viral lesions.

In a further preferred embodiment, the present invention also provides a method of treatment of viral lesions as described hereinabove, wherein the aforementioned plant extracts are supplemented by extracts of plants selected from the group consisting of *Uncaria tomentosa*, *Thymus vulgaris*, *Matricaria recutita*, *Salix alba*, *Calendula officinalis*, *Usnea barbata*, *Ligusticum porterii-osha*, *Gaultheria procumbens*, *Camellia sinensis*, *Vaccinium myrtillus*, *Melissa officinalis*, *Allium sativum*, *Camellia sinensis* and *Krameria triandra*.

In a particularly preferred embodiment, the present invention provides a method of treatment of mucosal and/or skin lesions of viral origin comprising the application of a therapeutically-effective amount of a mixture of extracts of the plant species *Echinacea purpurea, Sambucus nigra, Hypericum perforatum, Commiphora molmol* and *Uncaria tomentosa*.

In another preferred embodiment of the method of the invention, the extract of the at least one further plant is an extract of *Centella asiatica*. In one preferred embodiment of this aspect of the invention, the lesions to be treated are oral lesions associated with a disease selected from the group consisting of periodontal disease, gingivitis, aphthous ulceration, mechanical trauma, thermal trauma, lichen planus, bullous pemphigoid, pemphigus vulgaris, dermatitis herpetiformis, angular chelitis and recurrent herpes. In another preferred embodiment, the lesions to be treated are skin lesions. In one more preferred embodiment, the skin lesions to be treated are lesions arising from dermal trauma. In a further preferred embodiment, the lesions are insect bites. In another preferred embodiment of this aspect of the invention, the lesions to be treated are anal lesions associated with a disease selected from the group consisting of anal fissures, hemorrhoids and non-specific irritation.

In a further aspect, the present invention is directed to a method of inhibiting one or more matrix metalloproteinases in mucosal and/or skin lesions of a subject in need of such treatment, comprising the application of a therapeutically-effective amount of a mixture of extracts of the plant species *Echinacea purpurea, Sambucus nigra* and *Centella asiatica* to said mucosal and/or skin lesions and surrounding tissue. Preferably, the one or more matrix metalloproteinases are selected from the group consisting of matrix metalloproteinases 1 to 9. More preferably, the one or more matrix metalloproteinases are selected from the group consisting of matrix metalloproteinases 1, 2, 8 and 9. In a preferred embodiment of this aspect of the invention, the aforementioned inhibition of the one or more matrix metalloproteinases is used in the treatment of periodontal disease. In another preferred embodiment, the inhibition of the one or more matrix metalloproteinases is used in the treatment of aphthous ulceration.

In each of the above-described methods, the mixture of plant extracts used may further comprise extracts of plants selected from the group consisting of *Gotu kola, Uncaria tomentosa, Thymus vulgaris, Matricaria recutita, Salix alba, Calendula officinalis, Usnea barbata, Ligusticum porterii-osha, Gaultheria procumbens, Camellia sinensis, Vaccinium myrtillus, Melissa officinalis, Allium sativum, Camellia sinensis* and *Krameria triandra*.

In one preferred embodiment of the invention, the anti-viral compositions, medicaments and treatment methods are used in the treatment or management of viral lesions of the oral cavity.

In another preferred embodiment of the invention, the anti-viral compositions, medicaments and treatment methods are used in the treatment or management of perioral lesions of viral origin.

In yet another preferred embodiment of the invention, the anti-viral compositions, medicaments and treatment methods are used in the treatment or management of genital lesions of viral origin.

In yet another preferred embodiment of the invention, the anti-viral compositions, medicaments and treatment methods are used in the treatment or management of viral lesions caused by the Herpes simplex virus.

In yet another preferred embodiment of the invention, the anti-viral compositions, medicaments and treatment methods are used in the treatment or management of viral lesions of the skin.

In another aspect, the present invention also encompasses a method for inhibiting one or more matrix metalloproteinases in vitro, comprising contacting an effective amount of a mixture of extracts of the plant species *Echinacea purpurea, Sambucus nigra* and *Centella asiatica* with said one or more matrix metalloproteinases. In one embodiment of this aspect of the invention, the one or more matrix metalloproteinases to be inhibited are selected from the group consisting of matrix metalloproteinases 1 to 9. In another embodiment, the one or more matrix metalloproteinases to be inhibited are selected from the group consisting of matrix metalloproteinases 1, 2, 8 and 9.

All the above and other characteristics and advantages of the present invention will be further understood from the following illustrative and non-limitative examples of preferred embodiments thereof.

DETAILED DESCRIPTION OF PREFERRED EMBODIMENTS

Figure 1:
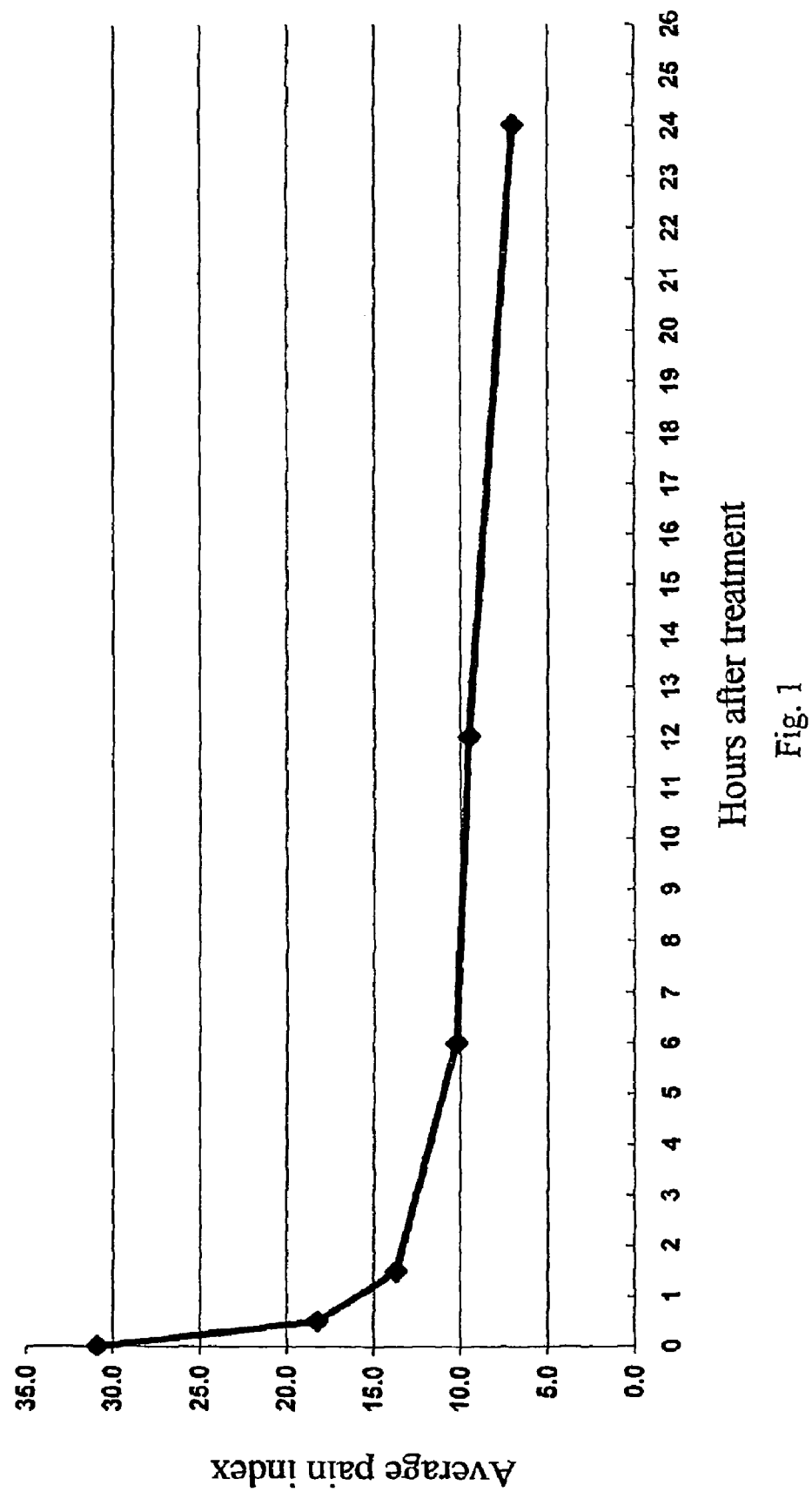
FIG. 1 graphically illustrates the reduction in ulcer-associated pain following treatment with an herbal composition of the invention.

The compositions and medicaments of the present invention are based on mixtures of plant extracts. It is to be noted that the term "extract" is used herein to include all of the many types of preparations containing some or all of the active ingredients found in the relevant plants. Thus the extracts may be produced by cold extraction techniques using a variety of different extraction solvents including, but not limited to, water, fatty solvents (such as olive oil), and alcoholic solvents (e.g. 70% ethanol). Cold extraction techniques are usefully applied to softer parts of the plant such as leaves and flowers, or in cases wherein the desired active components of the plant are heat labile. Alternatively, the aforementioned solvents may be used to produce extracts of the desired plants by a hot extraction technique, wherein said solvents are heated to a high temperature, the precise value of said temperature being dependent on the properties of the chosen solvent, and maintained at that temperature throughout the extraction process. Hot extraction techniques are more commonly applied to the harder, tougher parts of the plant, such as bark, woody branches and larger roots. In some cases, sequential extractions need to be performed in more than one solvent, and at different temperatures.

Standard procedures for producing plant extracts (including hot extraction, cold extraction and other techniques) are described in many publications including "Medicinal plants: a field guide to the medicinal plants of the Land of Israel (in Hebrew), author: N. Krispil, Har Gilo, Israel, 1986" and "Making plant medicine, author: R. Cech, pub. by Horizon Herbs, 2000".

Compositions and medicaments containing mixtures of extracts of different plant species, such as those of the present invention may be prepared using different ratios of each extract. For example, the antiviral medicaments and compositions of the present invention preferably comprise extracts of *Echinacea purpurea, Sambucus nigra, Commiphora molmol* and *Hypericum perforatum* in the following range of weight ratios:

2-6:2-4:3-6:2-6

More preferably, these components are present in the weight ratio of 4:3:5:4.

Similarly, the compositions of the invention used to treat mucosal diseases preferably comprise extracts of *Centella asiatica*, *Echinacea purpurea* and *Sambucus nigra* in the following range of weight ratios:
0.5-3:0.5-3:2:15

More preferably, these extracts are present in the weight ratio of 1.5:1.5:7

In order to treat a patient with a therapeutic composition or medicament containing a mixture of herbal extracts as described hereinabove, it is necessary to administer said composition or said medicament in a therapeutically-effective amount, that is, in an amount that will provide a concentration of the herbal extracts at the treatment site that is capable of exerting the desired therapeutic effect. It has been found, in general terms, that the compositions and medicaments of the present invention need to be administered in amounts such that, typically, each topical dose contains between 0.1 mg and 10 mg (dry weight) of each herbal extract, the precise values depending on the particular combination of extracts used, and on the mode of topical delivery. Thus, in the case of the therapeutic composition of the present invention that is used in the treatment of mucosal lesions, the weights of the original plant material used to prepare a controlled-release delivery device (as described in Example 2, hereinbelow) are:
*Centella asiatica* 1.6 mg
*Echinacea purpurea* 1.6 mg
*Sambucus nigra* 7.56 mg In the case of compositions and medicaments intended primarily for topical use (such as those of the present invention), it is necessary to administer said compositions and medicaments for periods of time that are sufficient to allow optimal contact of the therapeutically effective amounts of the herbal extracts with the lesions to be treated. When the compositions and medicaments are to be given by incorporation into a controlled-release intra-oral device (as described in Example 2 hereinbelow), said device needs to remain in contact with the lesion to be treated for a period of between 1 and 5 hours. This treatment may be repeated up to 5 times each day, as required, and as determined by a competent clinician.

Mouthwashes containing the compositions and medicaments of the present invention should be taken in quantities of between 5 ml and 15 ml and allowed to remain in contact with the lesions to be treated for periods of between 30 seconds and one minute. This treatment regime may be repeated up to 5 times per day.

Lozenges, pastilles, candies and other solid, soluble formulations are to be placed in the mouth, if possible in close proximity to the lesions to be treated, and allowed to dissolve at the natural rate determined by the additives present in said formulations.

The compositions and medicaments of the present invention as disclosed hereinabove and exemplified hereinabove may be prepared and delivered in a number of different forms.

In a preferred embodiment of the invention, medicaments and compositions are intended for topical application at the site of the mucosal lesion. Dosage forms suitable for topical application to mucosal surfaces include ointments, pastes, lotions, creams, mouthwashes, lozenges, candies, chewing gums, solutions, gels and sprays. Thus, in addition to the active ingredients, the compositions of the present invention may also contain excipients such as zinc, zinc oxide, silicones, calcium silicate, aluminum hydroxide, polyethylene glycols, fats of animal or vegetable origin, oils, waxes gums, starch and cellulose or cellulose derivatives.

In other embodiments of the invention, compositions for vaginal administration or for anal administration may be prepared by mixing the active plant-derived components with suitable non-toxic, non-irritating carriers such as suppository wax, polyethylene glycol or cocoa butter.

In a preferred embodiment of the invention, the compositions and medicaments are administered by means of a localized delivery system that allows topical release of the active constituents of said compositions and medicaments. Any suitable local delivery device may be used to administer the compositions and medicaments to the mucosal surface. However, in a particularly preferred embodiment of the invention the local delivery device is a slow release device such as illustrated hereinbelow in Example 2.

The following examples are provided for illustrative purposes and in order to more particularly explain and describe the present invention. The present invention, however, is not limited to the particular embodiments disclosed in the examples.

Example 1

Effect of the Anti-Viral Composition on the Formation of Viral Plaques In Vitro

Method:

The antiviral composition was prepared as follows: 2 ml of a 1:1 hydroalcoholic extract of *Echinacea purpurea* was mixed with 7.5 ml of a 1:5 hydroalcoholic extract of *Sambucus nigra*, 8 ml of a 1:4 hydroalcoholic extract of *Commiphora molmol*, 10 ml of a 1:4 preparation of a hydroalcoholic extract of *Uncaria tomentosa* and 20 ml of a 1:10 hydroalcoholic extract of *Hypericum perforatum*. The term "a 1:x hydroalcoholic extract" as used herein indicates that 1 gram of plant material was extracted with x volumes of the alcoholic extraction medium. In the case of all of the plant extracts used in the present example, the extraction medium was a "hydroalcohol". For the present purposes, the term "hydroalcohol" is defined as an aqueous solution of a lower alcohol. Preferably, the lower alcohol used was ethanol, which was generally prepared as a 50% solution. In some preparations, ethanol was prepared at a different aqueous dilution within the range of 25-90% (v/v), with respect to the ethanol. The weight ratio of *E. purpurea:S. nigra:C. molmol:U. tomentosa:H. perforatum* in this mixture is 4:3:4:5:4. The above-mentioned alcoholic extracts were purchased either from Herbal Apothecary, Syston, Leicester, U.K. or from Analit Extracts Ltd, M.P. Hefer 38100, Israel.

Disks of 3MM filter paper (Whatman Inc.) (5 mm diameter) were soaked in a solution of the compositions to be tested, and placed on a semi-solid agar-containing culture medium covering a monolayer of BSC-1 (green monkey kidney) cells infected with a partially confluent dose of either Herpes simplex type 1 virus (HSV-1) or Herpes simplex type 2 virus (HSV-2). Following 3-4 days incubation at 37° C., the cells were fixed with formaldehyde (20% aqueous solution) and stained with crystal violet (0.1% solution in 0.1M citric acid). The presence of a white color in the central area of the culture indicated toxic damage of the cultured cells due to the anti-viral compositions. Inhibition of viral plaque formation indicated that the composition tested possesses anti-viral activity.

Acyclovir (ACG), a known and commonly used drug against herpes viruses, was included in the assay as a positive control.

Results:
The results of a typical plaque assay are given below.

| Extract | Toxicity | anti-HSV1 | anti-HSV2 |
|---|---|---|---|
| Virosyn | 0-10 | 2-11 | 3-11 |
| Hypericum | 5 | 4-7 | 3-12 |
| Uncaria | 0 | 0-8 | 7-8 |

Note 1: Virosyn is the herbal composition described hereinabove comprising extracts of the following five plant species: *Echinacea purpurea, Hypericum perforatum, Commiphora molmol, Uncaria tomentosa* and *Sambucus nigra*.
Note 2: The numerical results in the above table are the diameters of the plaques (in mm) after treatment of the cell cultures with the disks soaked with extracts. Each virus inhibition or cell toxicity experiment was performed in triplicate.
Note 3: The toxicity of each extract was assessed by measuring the diameter of the blue-stained plaque in the center of cell cultures that did not receive virus.

The above results indicate that the herbal extract mixture tested possess antiviral activity for both HSV1 and with minimal toxicity to the cultured mammalian cells.

Example 2

Topical Slow-Release Device for Delivery of the Compositions to the Oral Mucosa

This example demonstrates the preparation of a slow-release device and the incorporation therein of a plant extract mixture containing *Centella, Echinacea* and *Sambucus*.

The slow release device consists of a mixture of carbomer (carbopol), hydroxypropyl cellulose and magnesium stearate blended as described hereinbelow. Magnesium stearate is used as a protective coating to reduce the solubility and adhesiveness of the device.

The device is prepared as follows:
1. The plant extract mixture is prepared by mixing 6 ml of a 1:4 hydroalcoholic extract of *Centella asiatica* with 1.5 ml of a 1:1 hydroalcoholic extract of *Echinacea purpurea* and 35 ml of a 1:5 hydroalcoholic extract of *Sambucus nigra*. The weight ratio of *C. asiatica:E. purpurea:S. nigra* in this mixture is 15:15:70. The hydroalcoholic extracts of *Centella asiatica* and *Echinacea purpurea* were purchased from Herbal Apothecary, Syston, Leicester, U.K., while the hydroalcoholic extract of *Sambucus nigra* was purchased from Analit Extracts Ltd., M.P. Hefer 38100, Israel. It is be noted that the abovementioned extract values of the form 1:x indicate that 1 g of the plant material was dissolved in x liters of solvent. The term "hydroalcoholic extract" indicates that the plant material was extracted using ethanol at concentrations of between 25% and 50% in water.
2. The plant extract mixture is mixed with 2 g sucrose and evaporated to dryness at 40° C. The residue is dissolved in 2 ml water, a further small volume of water added, and the solution lyophilized overnight.
3. A mixture of the carbomer compound Carbopol® 934 P (B.F. Goodrich, Cleveland, Ohio, USA) (2 g) and hydroxypropyl cellulose (Klucel Type HF, Hercules BV, Rijswijk, Holland) (1 g) is prepared by crushing the two components together.
4. A 1 g aliquot of the carbomer-hydroxypropyl cellulose mix (prepared in step 3.) is mixed together with 100 mg of the lyophilized plant extract powder (prepared in step 2).
5. Magnesium stearate (pharmaceutical grade, obtained from Riedel-De Haen, Germany) (1 g) is mechanically mixed with 2 g of the carbomer-hydroxypropyl cellulose mix.
6. 14 mg of the magnesium stearate-polymer mix (step 5.) is placed on the bottom of the plunger (13 mm diameter die manufactured by Perkin-Elmer, U.K.) of a mechanical press (Spex Industries, Mutuchen, N.J., USA) and overlaid with 70 mg of the plant extract-polymer mix (step 4.). Pressure (10 tons force) is applied for 30 seconds.

In addition to the active herbal ingredients, various flavorings, excipients and colorings may be added in order to modify the taste, consistency and color of the preparation.

The side of the device containing the herbal ingredients (i.e. the side not containing the magnesium stearate) is applied directly to the mucosal surface containing the lesion to be treated. Alternatively, the mucosal surface may be pre-moistened with water or saline before application of the device. Following application, the device is held in place with gentle pressure for approximately 10 seconds. After releasing the gentle pressure, the device adheres to the mucosal tissue for a period of up to five hours.

Depending on the mucosal lesion to be treated, the device containing the herbal mixture described hereinabove may be used several times per day (e.g. 3 times per day) for periods of between two days and one month.

Example 3

Use of an Herbal Composition of the Invention to Reduce the Pain Associated with Oral Mucosal Lesions A convenient, non-random sample of 57 dental patients presenting in a private dental clinic with painful oral ulcers of either traumatic or aphthous origin were treated by applying to the affected site a slow-release device containing a herbal composition of the invention (as described in Example 2 hereinabove). The device was left in place for a 24 hour period. The ulcer-associated pain experienced by the patients was recorded and expressed on a visual analog scale (S. Chrubasik et al. (2000) Am. J. Med. 109: 9-14), as depicted in FIG. 1. The clinical correlates of the pain index values used in this scale are as follows: 0=no pain; 50=requires analgesic; 100=requires anesthetic. The highest recorded pain index reported by an individual patient in this study was 90.

It may be seen from these results that the patients experienced an almost immediate decrease in pain (with a mean decrease of greater than 50%). This decrease in pain levels continued over the following 6 hours, achieving a mean pain decrease of greater than 70%. The painful symptoms did not recur following cessation of treatment.

Example 4

Effect of an Herbal Composition of the Invention on the Size of Mucosal Lesions

Operating as in the study presented in Example 3, the effect of the herbal composition used therein on the healing of the oral ulceration experienced by the patients was determined by quantification of lesion size using a Scion image analysis system. Briefly, lesions were photographed and digitized using a digital camera and associated Smartcard. The image files obtained thereby were processed using the Photoshop software package (Adobe Systems Inc.) running in Microsoft Windows ME on an IBM-compatible personal computer. The periphery of each lesion was outlined and copied into a new window of the NIH Image software package (National Institutes of Health, Bethesda, Md.), where, following thresholding, the lesion area was automatically calculated.

Results from a sequential study of 45 patients with oral ulceration demonstrate that the treatment with the herbal composition caused a mean 60% decrease in lesional size over a 24-36 hour period.

Example 5

Anticollagenase Activity of an Herbal Composition of the Invention

Anticollagenase Testing:
Procedure:

Protease activity was assessed on gelatin zymograms. Twelve percent polyacrylamide gels (0.75 mm thickness) were cast containing 10% gelatin as a substrate for the collagenase enzymes, which were applied to the gels under non-reducing conditions without heating. The gels were run, soaked in 200 ml of 2% Triton X-100 in distilled water on a gyratory shaker (0.5 hours, 20° C.), and incubated in developing buffer (50 mM Tris [pH 8.0], 1 mM $CaCl_2$), unless otherwise indicated, for 15 hours at 37° C. The gels were examined following staining with Coomassie blue. Protease activity shows up as clear bands (indicative of cleavage of the gelatin substrate) on a blue background. For inhibition studies, either specific protease inhibitors (DFP (1 Mm), EDTA (5 Mm), BBI (10 mg/ml), phenylmethyl sulfonyl fluoride (PMFS) (50 Mm) or tetracyclines (0.1 and 0.25 Mm)) or a composition comprising a mixture of Echinacea purpurea, Sambucus nigra and Centella asiatica (prepared as described in Example 2, hereinabove) were added to the developing buffer after the run but before the gel was incubated in said developing buffer. In the latter case, the herbal composition was added to the buffer at a concentration of one volume composition to 50 volumes buffer. To determine protease activity as a function of pH, samples were run on zymograms and subsequently incubated in the appropriate buffer (50 Mm citrate-phosphate buffer [pH 5], 50 Mm ADA buffer [pH 6 and 7], 50 Mm TRIS [pH 8 and 9] or 50 Mm CAPS [pH 10]), containing 1 Mm $CaCl_2$.

Results:

Preliminary findings have demonstrated strong inhibitory effects of low concentrations of the herbal extracts on a cocktail of proteases (containing high concentrations of matrix metalloproteinases 2, 3, 8 and 9). These results demonstrate a direct inhibitory effect of low doses of herbal extracts on common metalloproteinases.

Figure 2:
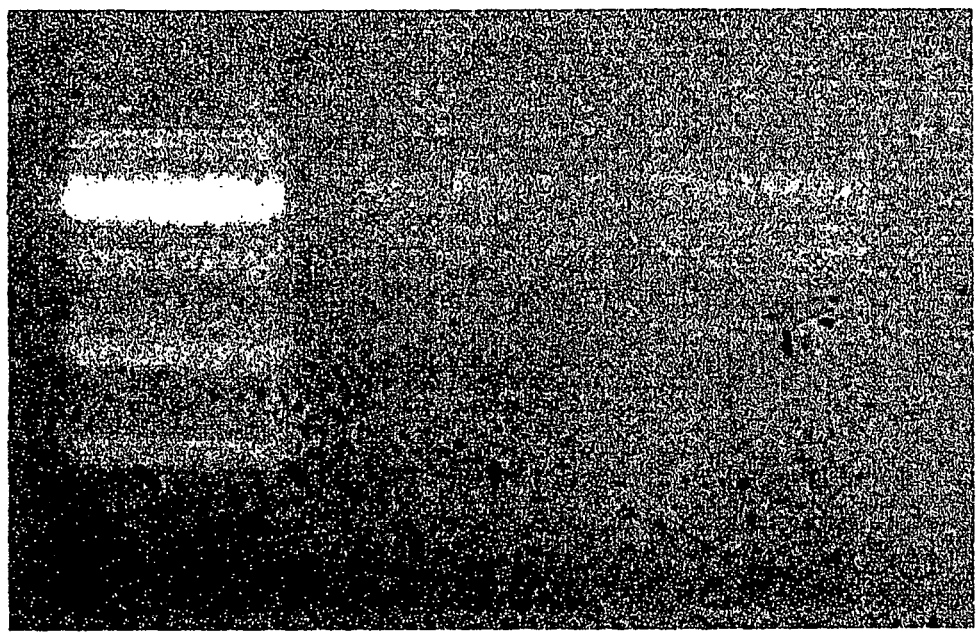
FIG. 2 shows a typical gelatin zymogram indicating the inhibitory effects of composition of the invention on the activity of a mixture of matrix metalloproteinases.

Representative results are shown in the gelatin zymogram depicted in FIG. 2, in which active proteases are indicated as white bands on a dark background. Line 1: 50 ng active metalloproteases are clearly detectable. Line 2 demonstrates definitive inhibition of the same metalloprotease cocktail present in line 1 by a 1/50 dilution of the aforementioned herbal composition.

Example 6

In Vivo Treatment of Gingival Inflammation Using an Herbal Composition of the Invention Effects on MMP Activity This study forms part of a controlled double-blind matched-sample (sixteen patients), three part clinical trial of the use of a herbal composition of the invention in controlling gingival inflammation 1, 4 and 7 days after placement of a transmucosal adhesive patch containing a composition containing Echinacea purpurea, Sambucus nigra and Centella asiatica (prepared as described in Example 2, hereinabove).

In the control subjects, a placebo treatment comprising a transmucosal adhesive patch containing food color was used.

Gingival Tissue removed during periodontal surgery was immediately placed on ice and subsequently frozen and stored at −80 degrees C., prior to performing matrix metalloproteinase (MMP) activity analysis thereon, as described hereinabove in Example 5. The gingival samples are prepared for this analysis by homogenizing the thawed tissue in PBS and centrifuging [10000 g×10 min].

The preliminary results obtained (data not shown) demonstrate that bands were found in the areas consistent with MMP 2, 9 which have been identified as proteases associated with periodontal disease. Tissue samples taken from the experimental sites showed no protease activity, indicating complete inhibition by the herbal composition of the invention.

Example 7

Figure 3:
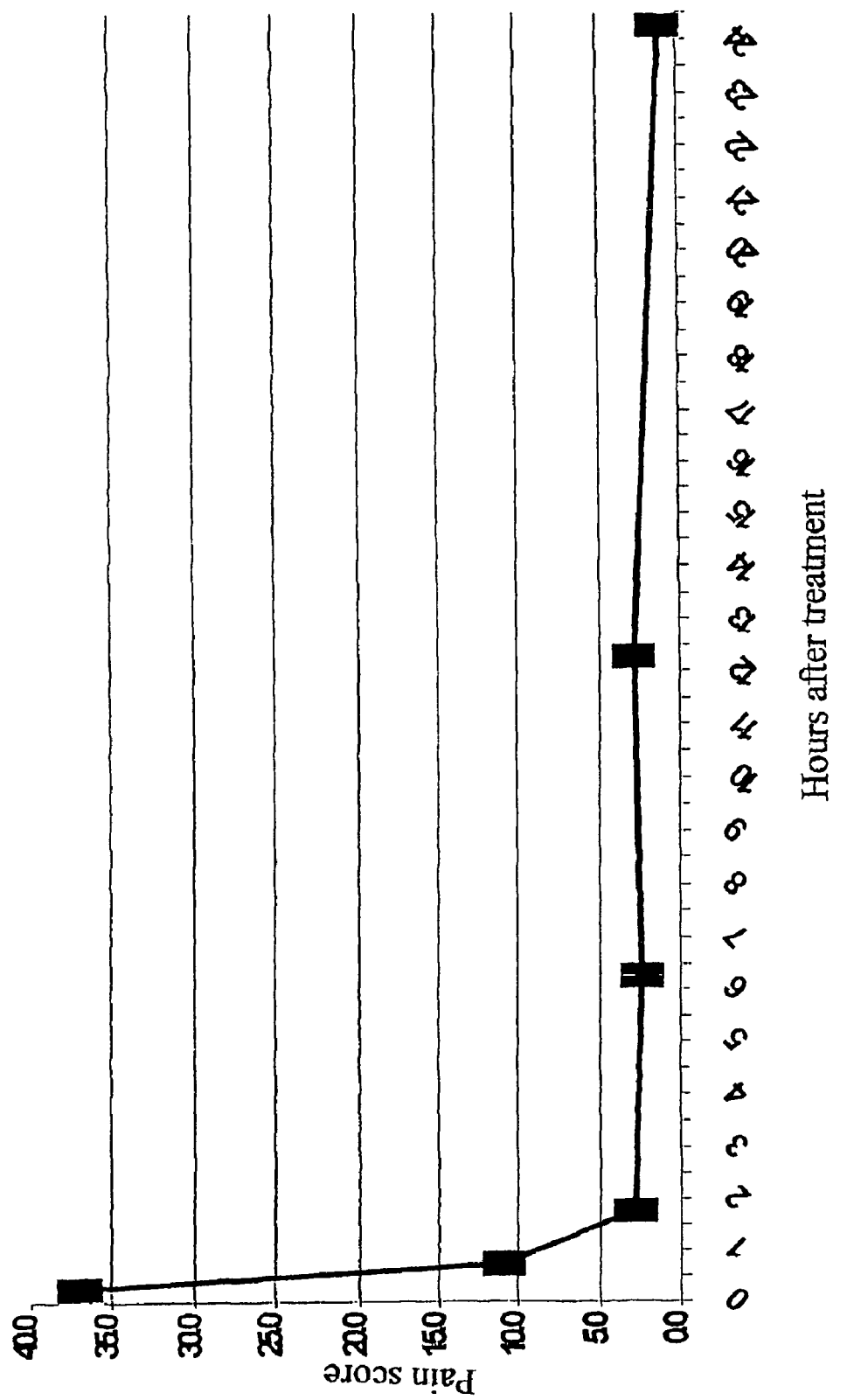
FIG. 3 graphically illustrates the reduction in insect bite-associated pain and irritation following treatment with an herbal composition of the invention.

In Vivo Effect of an Herbal Composition of the Invention on Localized Irritation Following an Insect Bite A subject having a painful insect bite on the skin overlying the upper arm was treated for a period of 24 hours with an adhesive patch comprising a composition containing Echinacea purpurea, Sambucus nigra and Centella asiatica (prepared as described in Example 2, hereinabove). The insect bite-associated pain experienced by the patient was recorded and expressed on a visual analog scale, as depicted in FIG. 3. The clinical correlates of the pain index values used in this scale are as follows: 0=asymptomatic; 50=requires medication; 100=extreme localized discomfort. The highest recorded pain index reported in this study was 38.

It may be seen from these results that almost instantaneous relief of the localized irritation was obtained.

Formulations

The following formulations comprising herbal compositions of the invention are given for purposes of illustration and exemplification only, and are not intended to limit the scope of the invention in any way. Thus, both the concentration of active ingredient within each formulation may be changed without removing said formulation from the scope of the invention. Similarly, other formulations comprising the herbal compositions claimed herein that contain different carriers, diluents, excipients, colorings, flavorings and other additives are still to be considered to be within the scope of the present invention.

The term "Active ingredient" used in the following formulation tables refers to any combination of herbal extracts that are within the scope of the invention. The weight percentage of the active ingredient is calculated in terms of the dry weight of the herbal composition. Representative examples of such combinations are:

A) composition comprising Echinacea purpurea, Hypericum perforatum, Commiphora molmol, Uncaria tomentosa and Sambucus nigra in a weight ratio of 4:4:4:5:3.

B) composition comprising *Echinacea purpurea, Sambucus nigra* and *Centella asiatica* in a weight ratio of 15:70:15.

Formulation 1

Mouthwash

| Ingredient | % by weight |
|---|---|
| Active ingredient | 0.15 |
| Glycerin, U.S.P | 10.000 |
| Ethanol, 190-proof, U.S.P | 7.500 |
| Flavor | 0.040 |
| Polyoxythylene (20) sorbitan monoisostearate | 0.200 |
| Sodium saccharin, N.P. | 0.050 |
| Boric acid, U.S.P | 0.075 |
| FD&C Green (1% solution) | 0.045 |
| Distilled water | balance |

Formulation 2

Lozenge

| Ingredient | % by weight |
|---|---|
| Active ingredient | 0.25 |
| Sorbitol | 17.5 |
| Mannitol | 17.5 |
| Starch | 13.6 |
| Sugar substitute | 1.2 |
| Flavor | 11.7 |
| Color | 0.1 |
| Corn syrup | Balance |

Formulation 3

Chewing Gum

| Ingredient | % by weight |
|---|---|
| Active ingredient | 0.25 |
| Gum base (30 parts Eastergum, 45 parts Coumarone resin, 15 parts dry latex, 10 parts Paraffin wax) | 30.00 |
| Sugar | 50.00 |
| Corn syrup | 18.00 |
| Citric acid | 1.00 |
| Flavor | balance |

Formulation 4

Toothpaste

| Ingredient | % by weight |
|---|---|
| Active ingredient | 0.5 |
| Sorbitol | 33.00 |
| Saccharin | 0.46 |
| Silica | 22.00 |
| NaF | 0.243 |
| Glycerin | 9.00 |
| NaOH (50%) | 0.20 |
| Carbopol | 0.20 |
| Keltrol | 0.60 |
| TiO$_2$ | 0.50 |
| Sodium alkyl sulphate (28% solution) | 4.00 |
| PEG 6 | 3.00 |
| FD&C Blue# 1 (1% solution) | 0.05 |
| Flavor | 1.1 |
| Water | Balance |

While specific embodiments of the invention have been described for the purpose of illustration, it will be understood that the invention may be carried out in practice by skilled persons with many modifications, variations and adaptations, without departing from its spirit or exceeding the scope of the claims.

What is claimed is:

1. A method of treatment of mucosal lesions comprising the therapeutically-effective amount of a mixture of extracts of the plant species *Echinacea purpurea Sambucus nigra* and *Centella asiatica* to the mucosal lesions and surrounding tissue of a subject in need of such treatment.

2. A method of treatment according to claim 1, wherein the mucosal lesions are oral lesions associated with a disease selected from the group consisting of periodontal disease, gingivitis, aphthous ulceration, mechanical trauma, thermal trauma, lichen planus, bullous pemphigoid, pemphigus vulgaris, dermatitis herpetiformis, angular chelitis and recurrent herpes.

3. A method of treatment according to claim 1, wherein the mucosal lesions are anal lesions associated with a disease selected from the group consisting of anal fissures, hemorrhoids and non-specific irritation.

4. A method of inhibiting one or more matrix metalloproteinases in mucosal and/or skin lesions of a subject in need of such treatment, comprising the application of a therapeutically-effective amount of a mixture of extracts of the plant species *Echinacea purpurea, Sambucus nigra* and *Centella asiatica* to said mucosal and/or skin lesions and surrounding tissue.

5. A method according to claim 4, wherein the one or more matrix metalloproteinases are selected from the group consisting of matrix metalloproteinases 1 to 9.

6. A method according to claim 5, wherein the one or more matrix metalloproteinases are selected from the group consisting of matrix metalloproteinases 1, 2, 8 and 9.

7. A method according to any one of claims 4, 5 and 6, wherein the inhibition of the one or more matrix metalloproteinases is used in the treatment of periodontal disease.

8. A method according to any one of claims 4, 5 and 6, wherein the inhibition of the one or more matrix metalloproteinases is used in the treatment of aphthous ulceration.

9. A method according to any one of claims 2 to 6, wherein the mixture of plant extracts further comprises extracts of plants selected from the group consisting of *Gotu kola, Uncaria tomentosa, Thymus vulgaris, Matricaria recutita, Salix alba, Calendula officinalis, Usnea barbata, Ligusticum porterii-osha, Gaultheria procumbens, Camellia sinensis, Vaccinium myrtillus, Melissa officinalis, Allium sativum, Camellia sinensis* and *Krameria triandra*.

10. A method for inhibiting one or more matrix metalloproteinases in vitro, comprising contacting an effective amount of a mixture of extracts of the plant species *Echinacea*

*purpurea, Sambucus nigra* and *Centella asiatica* with said one or more matrix metalloproteinases.

11. A method according to claim 10, wherein the one or more matrix metalloproteinases to be inhibited are selected from the group consisting of matrix metalloproteinases 1 to 9.

12. A method according to claim 11, wherein the one or more matrix metalloproteinases to be inhibited are selected from the group consisting of matrix metalloproteinases 1, 2, 8 and 9.

13. A method of treatment of skin lesions comprising the application of a therapeutically-effective amount of a mixture of extracts of the plant species *Echinacea purpurea, Sambucus nigra* and *Centella asiatica* to the skin lesions and surrounding tissue of a subject in need of such treatment.

* * * * *